United States Patent [19]

Carlson

[11] Patent Number: 5,003,608
[45] Date of Patent: Mar. 26, 1991

[54] APPARATUS AND METHOD FOR MANIPULATING DEVICES IN ORIFICES

[75] Inventor: Jason L. Carlson, Redwood City, Calif.

[73] Assignee: Resound Corporation, Redwood City, Calif.

[21] Appl. No.: 410,978

[22] Filed: Sep. 22, 1989

[51] Int. Cl.$^5$ .............................................. H04R 25/02
[52] U.S. Cl. ...................................... 381/68.6; 381/68; 381/69; 128/420.5
[58] Field of Search ................. 381/68, 68.6, 69, 69.1, 381/69.2; 248/690; 16/110.5, 115; 220/94 R; 600/25, 32; 623/10; 128/420.5, 420.6, 746; 181/130, 135; 73/585

[56] References Cited

U.S. PATENT DOCUMENTS

| | | | |
|---|---|---|---|
| 4,565,904 | 1/1986 | Harada | 381/68.6 |
| 4,756,312 | 7/1988 | Epley | 381/68.6 |

*Primary Examiner*—Jin F. Ng
*Assistant Examiner*—M. Nelson McGeary, III
*Attorney, Agent, or Firm*—McCubbrey, Bartels, Meyer & Ward

[57] ABSTRACT

The present invention comprises an apparatus and method for inserting into, orienting within, and withdrawing from an ear a hearing aid, earphone, transducer, microprocessor, radio, sensor, or other mechanical or electronic device. The apparatus includes a housing attached to and containing the device. The housing has slots in which a handle, which is secured inside the housing, can slide. A magnet placed proximate the handle causes the handle to slide out, away from the housing, making it easy to grasp. The device can thus be inserted in, oriented within, or withdrawn from the ear by use of the handle. In its rest position, the handle lies flush against the housing making it almost visually imperceptible.

9 Claims, 2 Drawing Sheets

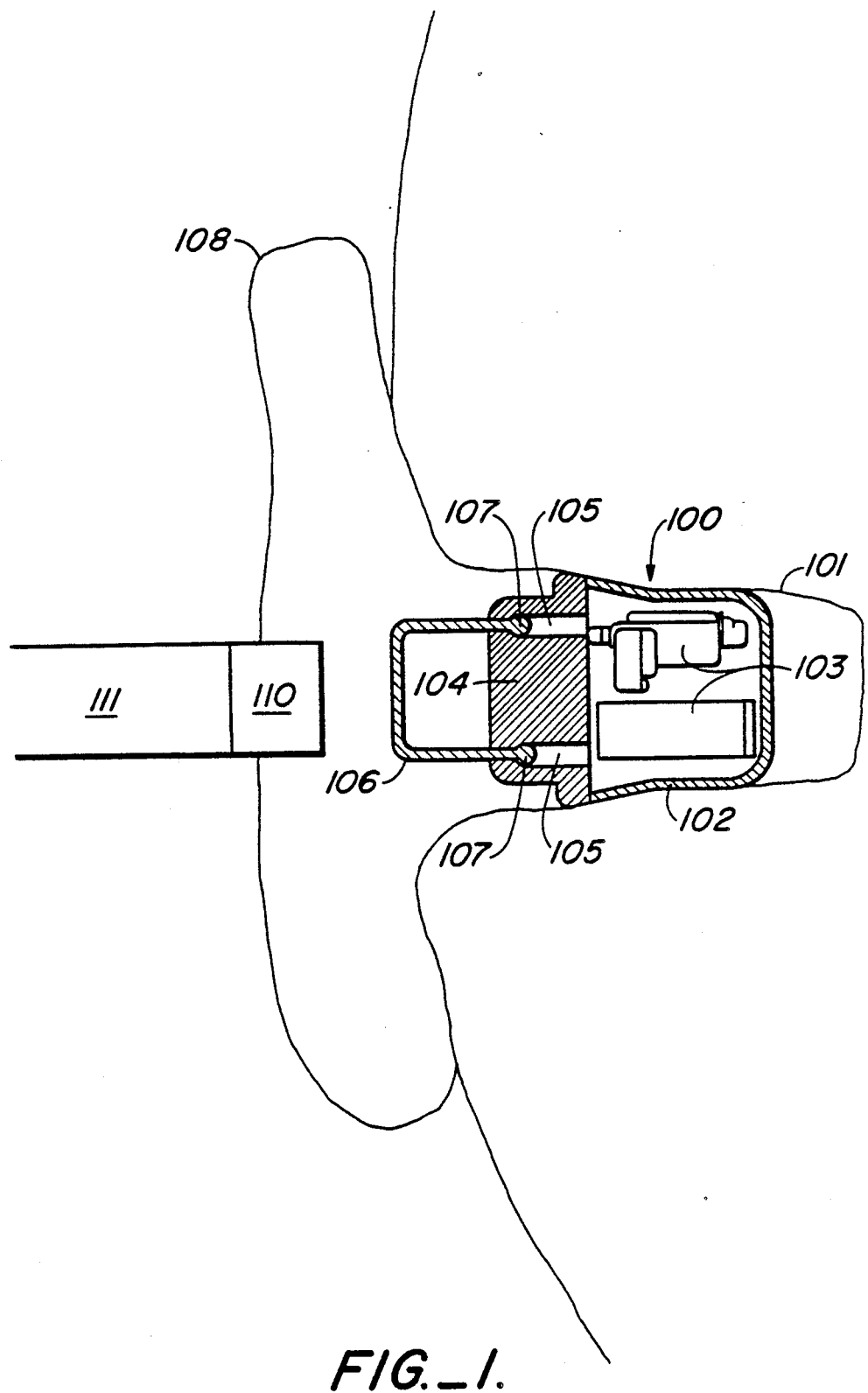
FIG._1.

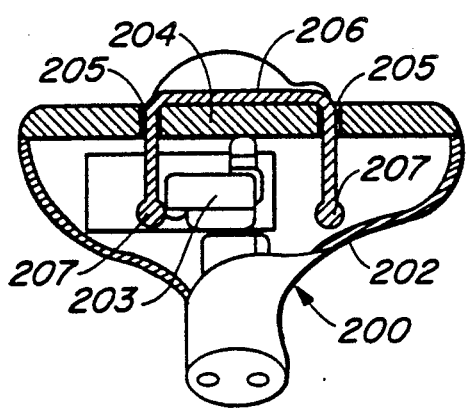
FIG._2.
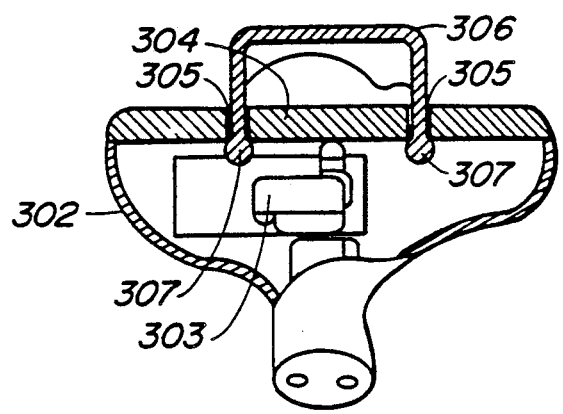
FIG._3.
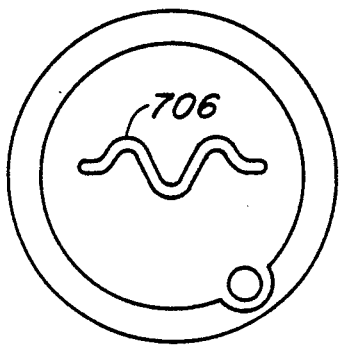
FIG._7.
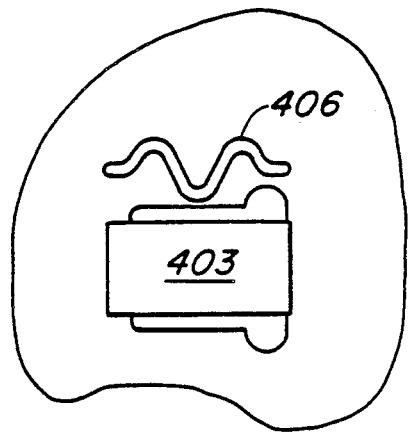
FIG._4.
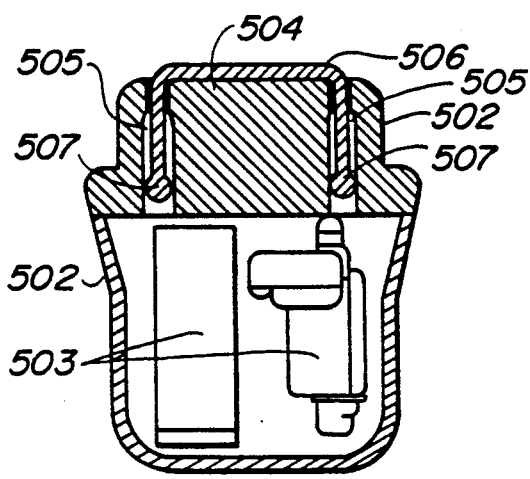
FIG._5.
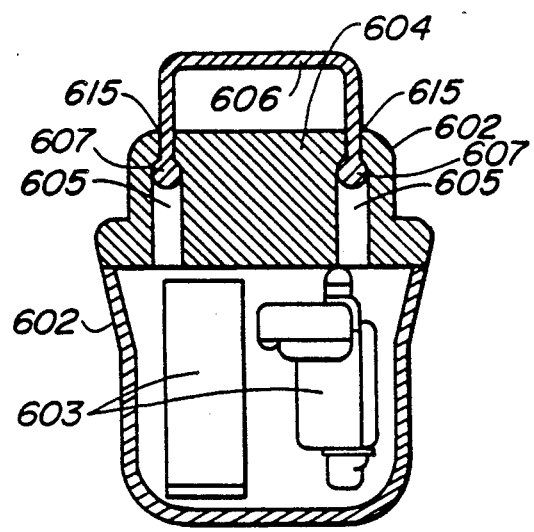
FIG._6.

APPARATUS AND METHOD FOR MANIPULATING DEVICES IN ORIFICES

FIELD OF THE INVENTION

The present invention relates generally to the field of the manipulation of deeply-seated devices in orifices and more particularly to the field of the insertion, orientation, and withdrawal of devices in the ear.

BACKGROUND OF THE INVENTION

The modern development of hearing aids provided devices which could be disposed entirely within the ear. Earlier hearing aids, however, typically extended out of the inner ear to the auricle, that part of the external ear which is outside of the head. That extended portion of the hearing aid was quite visually evident, which was cosmetically and aesthetically undesirable. Electronic miniaturization has allowed in-the-ear hearing aid devices to be disposed within the ear's canal, greatly improving the sensitivity and sound quality of the devices, and importantly, also making them almost visually undetectable. Further progress in the art and science of improving the auditory abilities of the hearing impaired provided canal recontour medical procedures which allowed hearing aid devices to be even more deeply seated and snugly fitted, thereby further improving sound quality.

Concomitant with the progress in hearing aid technology have come problems in properly inserting and withdrawing devices which are becoming smaller and smaller. Many in-the-canal hearing aids extend no farther than the tragus (the cartilaginous projection anterior to the external opening of the ear) and smaller devices extend only to the bottom of the concha (external ear). The relatively larger early in-the-ear hearing aids were more easily inserted and withdrawn since they extended well past the tragus. However, newer hearing aids, and particularly the in-the-canal devices, are smaller and purposely designed not to extend out beyond the bottom of the concha. Thus, the proper insertion and withdrawal of such devices by the user can be extremely difficult. This may be a particular problem because the hearing impaired are often elderly and may have limited manual dexterity and tactile sensitivity. The difficulties of insertion and removal may even require assistance from another individual, which requirement obviously diminishes a user's independence. Furthermore, if tools or implements are employed, the hearing aid may be damaged or the ear itself may be injured.

One prior art approach to this problem is disclosed in U.S. Pat. No. 4,565,904 to Harada which utilizes a hinged handle with a bulbous tip for easy grasping. The handle folds inwardly to decrease its outward projection from the hearing aid thereby rendering it less visible. To remove the hearing aid from the ear, the user grasps the bulbous portion of the handle and exerts an outward pull, thereby allowing the handle to pivot outwardly around its hinge. Thereafter, the handle may be regrasped and pulled to remove the attached hearing aid from the ear.

Harada's device is simple and operates effectively if the hearing aid is not very deeply seated in the ear. For deeply-seated in-the-canal devices, the stem of the handle would have to be quite long in order to extend outwardly from the ear a sufficient distance to be graspable. This would cause problems in stowing the handle in its folded position since the length of the stem is necessarily limited by the cross-sectional dimensions of the hearing aid. Further, the requirement that the handle be flipped up out of its folded position before it can be grasped requires a relatively high degree of touch sensitivity and manual dexterity which, as mentioned, elderly individuals may not possess. Another problem may arise on insertion and removal of the hearing aid using this invention. The handle, being a lever attached to a single fulcrum at the hearing aid body, when grasped and pulled or pushed may take the hearing aid out of its proper alignment, thereby causing pain or injury to the ear.

Another prior art approach is disclosed in U.S. Pat. No. 4,756,312 to Epley which utilizes a magnetic attachment apparatus comprising a magnetic coupling element attached to the hearing aid and an inserter probe for engagement of the coupling element. In one embodiment of Epley's device, a rotatable magnet with a dial for changing the polarity of the magnetic field is attached to the inserter probe. A holder ring, also having a magnet, is secured to the hearing aid. An orientation bar on the holder ring and an orientation slot on the inserter probe must be matched to provide proper orientation of the hearing aid within the ear. Upon insertion, the magnetic fields of the inserter probe and the holder ring must be such that there is attraction between the ring and the inserter. After coupling of the orientation bar and slot, the dial on the inserter probe is rotated so that the magnetic fields produce a neutral release position. Then the inserter probe can disengage from the holder ring and the inserter probe may be withdrawn from the ear leaving the hearing aid inside the ear. To remove the hearing aid, the inserter probe is inserted into the ear until its orientation slot engages the orientation bar, then the dial on the inserter bar is rotated to its attraction position so that the holder ring is now magnetically attached to the inserter probe and the hearing aid may be removed from the ear. In another embodiment of Eplye's invention, a bipolar magnetic attachment device provides a stronger magnetic attachment by utilizing a pair of curved magnetic stator plates with tapered extensions. A rotatable magnet is again deployed on the coupling element to provide variable polarity. When the proper electrical contacts are made, a magnetic circuit is completed and the coupling element and the attachment device are strongly held in magnetic attraction. Again, release of the attachment device is accomplished by setting the dial for a neutral magnetic field and removal of the hearing aid is achieved by rotating the dial to produce an attractive magnetic field. A cam and cam follower with support cylinder are provided for detent orientation of the magnet for attraction or release.

Eplye's device is relatively large, complex, and somewhat operationally complicated. This is partially attributable to the magnetic requirements of his direct contact hearing aid which utilizes electromagnetic sensors. The employment of a magnetic field alone to remove the hearing aid of necessity requires a relatively massive ferromagnetic metallic mass on the hearing aid in order to produce a sufficient field to pull the hearing aid out of the ear. This metallic mass undesirably contributes to the size and weight of the hearing aid. The relatively strong magnetic fields also potentially interfere with the proper electronic functions of the hearing aid and thus the components must be carefully shielded.

The requirements of orienting the bar and slot for coupling the probe and rotating the dial to adjust the field make insertion and removal rather complicated. Again, elderly hearing aid users may have some difficulty with such procedures.

There is, therefore, a need for a small, simple yet effective apparatus capable of quickly and efficiently inserting and removing from the ear hearing aids and other like devices, particularly deeply-seated in-the-canal devices, and such an apparatus represents a significant advance in the art.

SUMMARY OF THE INVENTION

It is a principal object of the present invention to provide a simple yet effective means for inserting, orienting, and removing a device from an orifice.

It is a further object of the present invention to provide a means for inserting, orienting, and withdrawing deeply-seated devices from the ear's canal.

It is another object of the present invention to provide a simple yet effective method for inserting, orienting, and withdrawing a device from an orifice.

It is yet another object of the present invention to provide a method for inserting, orienting, and withdrawing deeply-seated devices from the ear's canal.

Broadly, the present invention comprises an apparatus and method for inserting into, orienting within, and withdrawing from an orifice a hearing aid, earphone, radio, transducer, sensor, microprocessor or other mechanical or electronic device. The apparatus includes a housing attached to and containing the device. The housing has slots in which a handle, which is secured inside the housing, can slide. A magnet placed proximate the handle causes the handle to slide out, away from the housing, making it easy to grasp. The device can thus be inserted into, oriented within, or withdrawn from the ear by use of the handle. In its rest position, the handle lies flush against the housing making it practically imperceptible.

The present invention provides a simple means and method for manipulating a device within an ear. Because of its simple design and the fact that the magnet is not an integral part of the device when in place in the ear (being utilized only when needed) the present invention is extremely small in size thereby contributing very little to the size of the device to which it is attached. This achieves the desirable aesthetic effect of unobtrusiveness. For devices deeply-seated within the ear, such as in-the-canal hearing aids and in particular for devices for insertion into medically recontoured canals, the present invention allows simple insertion, removal and manipulation of the devices without requiring particular manual dexterity or tactile sensitivity.

A further understanding of the nature and advantages of the present invention may be realized by reference to the remaining portions of this application and the attached drawings.

BRIEF DESCRIPTION OF THE DRAWINGS

FIG. 1 illustrates an embodiment of the present invention attached to a deeply-seated in-the-canal hearing aid disposed in an ear canal.

FIG. 2 illustrates an embodiment of the present invention with its handle in a rest position attached to an in-the-ear hearing aid.

FIG. 3 illustrates an embodiment of the present invention with its handle in an extended position attached to an in-the-ear hearing aid.

FIG. 4 is a top view of an embodiment of the present invention for in-the-ear hearing aids showing a handle having a curved "M" shape.

FIG. 5 illustrates an embodiment of the present invention with its handle in a rest position attached to an in-the-canal hearing aid.

FIG. 6 illustrates an embodiment of the present invention with its handle in an extended position attached to an in-the-canal hearing aid.

FIG. 7 is a top view of an embodiment of the present invention for in-the-canal hearing aids showing a handle having a curved "M" shape.

DETAILED DESCRIPTION OF THE INVENTION

The preferred embodiment of the present invention is illustrated schematically in FIG. 1. A hearing aid 100 is deeply-seated in a user's ear canal 101. Such a hearing aid is manufactured by Resound Corporation of Redwood City, Calif., Model PHS2. A housing 102 contains the workings 103 of hearing aid 100 and a battery compartment 104. Placed along the sides of battery compartment 104 are slots 105 in which a "U"-shaped handle 106 having bulbous ends 107 is slidably disposed. Slots 105 are tapered in a direction away from workings 103 so that bulbous ends 107 of handle 106 contact the walls of slots 105, thereby securing handle 106 to housing 102 when handle 106 is in an extended position away from housing 102. When a magnet 110 attached to a holder 111 is placed near the opening of ear 108, handle 106, being constructed of a material susceptible to magnetic attraction, assumes the extended position away from housing 102. In this position, handle 106 may be easily grasped by the user to insert, orient, and withdraw hearing aid 100.

The method of utilization of the present invention includes procedures for insertion, manipulation or orientation, and withdrawing of devices in orifices.

For insertion, magnet 110 is placed proximate handle 106 causing handle 106 to assume its extended position. Handle 106 now may be easily grasped for insertion into an orifice. For manipulation and orientation, handle 106 is in its extended position and from the orientation of handle 106 may be determined the orientation of the device to which it is attached. Thus the device may be manipulated with knowledge of relative orientation. For withdrawal, magnet 110 is placed proximate handle 106 causing handle 106 to assume its extended position. Handle 106 is easily grasped for withdrawal. Because the relative orientation of handle 106 is known from tactile sensation, the orientation of the attached device is also known and care may be taken not to damage the device or injure the orifice.

Because handle 106 may be slid in slots 105 towards housing 102, handle 106 can lie as deeply within ear 108 as hearing aid 100, and since magnet 110 is employed only when needed to extend handle 106, the present invention achieves the desired aesthetic effect of being practically undetectable. The manipulation apparatus of the present invention adds very little to the size of the hearing aid since handle 106 is placed along the sides of battery compartment 104. Thus, the simple and elegant design of the present invention effectively achieves its mechanical objective while maintaining a small size and desirable unobtrusiveness.

Another embodiment of the present invention for application to in-the-ear hearing aids or other like devices is illustrated in FIGS. 2, 3, and 4. Such in-the-ear hearing aids are manufactured by Resound Corporation of Redwood City, Calif., Model PHS1.

FIG. 2 shows in-the-ear hearing aid 200 having a housing 202 containing hearing aid workings 203 and having slots 205. A handle 206 is slidably disposed in slots 205 and has bulbous ends 207 within housing 202. Handle 206 is shown in its rest position lying flush against housing 202, thereby achieving desirable small size and unobtrusiveness.

FIG. 3 shows handle 306 in an extended position away from housing 302 with bulbous ends 307 secured by slots 305 and the inside surfaces of housing 302. In the extended position, handle 306 is easily accessible for grasping.

FIG. 4 shows a top view of this embodiment of the present invention. Handle 406 has a curved "M" shape for tactile feedback, thereby providing easy manipulation, and for greater metallic mass to increase magnetic attraction. In the preferred embodiment, handle 406 is constructed from piano wire to provide magnetic sensitivity and light weight.

Another embodiment of the present invention for application to in-the-canal hearing aids is shown in FIGS. 5, 6, and 7. The hearing aid in this embodiment is essentially the same as in FIG. 1. FIG. 5 shows handle 506 in its rest position flush against housing 502. FIG. 6 shows handle 606 in its extended position away from housing 602. Bulbous ends 607 have been pulled upwards to abut regions 615 of smaller diameter of slots 605, thereby causing handle 606 to be secured to housing 602. FIG. 7 is a top view of this embodiment showing a handle 706, constructed from piano wire, in a curved "M" shape for tactile feedback and greater mass.

In summary, an apparatus and method for insertion, orientation, and withdrawal of a device from an orifice has been described. The simple and elegant design and concept of the present invention provides a small sized, unobtrusive yet effective means and method for manipulating a device which may be difficult to otherwise reach. Because the magnet is utilized only when needed to extend the handle and the handle lies flush against the housing, the present invention adds very little to the size of the device to be manipulated. Further, the present invention is shaped and sized to provide easy handling and tactile feedback requiring no particular manual dexterity. Finally, the present invention provides a means to reach and manipulate devices very deeply-seated in the orifice.

While the above description has been made with reference to hearing aids of various kinds, it is understood that the present invention may be embodied in any device for the insertion into, orienting within, or withdrawing from any orifice. For example, the present invention is applicable to electronic and mechanical devices such as earphones, radios, microprocessors, light probes, surgical instruments, transducers, transponders, speakers, or sensors of any kind. In other words, the present invention is applicable to any device which may require some means of manipulation. The orifices may be organic, naturally occurring, or mechanical.

While the above description provides a full and complete description of the preferred embodiments of the present invention, various modifications, alternate constructions and equivalents may be employed. Therefore, the above description and illustrations should not be construed as limiting the scope of the invention which is defined solely by the following claims.

I claim:

1. An electronic device adapted for positioning within the auditory canal or other body orifice and including means for inserting into, orienting within, and withdrawing said device from the orifice by means of a magnet, said device comprising:
   a housing having at least one slot therein,
   and a handle for grasping said device, slidably disposed in said slot in said housing,
   magnet means separate from said handle;
   said handle being oriented such, as to slide within said slot when said magnet means is brought adjacent thereto to enable manipulation of said device.

2. The apparatus of claim 1 wherein said housing has two slots being tapered towards the outside of said housing, and said handle being "U" shaped with bulbous ends of the "U" sized so that when said handle is extended away from said housing, said handle is secured by said bulbous ends contacting the tapered portion of said slots proximate the outside of said housing thereby securing said handle to said housing to prevent withdrawal of said handle fully from said slots.

3. The apparatus of claim 2 wherein the central section of said "U"-shaped handle has a curved "M" cross-section.

4. The apparatus of claim 1 wherein said central section of said handle lies flush against said housing when in a rest position.

5. The apparatus of claim 1 wherein said housing has two slots, and said handle being "U" shaped with bulbous ends of the "U" disposed inside said housing and sized so that when said handle is extended away from said housing, said bulbous ends contact the ends of said slots inside said housing thereby securing said handle to said housing.

6. The apparatus of claim 1 wherein said orifice is an ear.

7. A method for withdrawing from an ear a hearing aid, earphone, transducer, microprocessor, radio, sensor, or other mechanical or electronic device, utilizing an apparatus comprising a housing, said housing containing the device having at least one slot therein, a handle for grasping slidably disposed in said slot and secured to said housing, and a magnet for causing said handle to slide within said slot, said method comprising the steps of:
   disposing said magnet proximate said handle causing said handle to slide in said slot towards said magnet; and
   withdrawing said apparatus from the ear by grasping said handle and pulling said housing containing the device.

8. A method for orienting within an ear a hearing aid, earphone, transducer, microprocessor, radio, sensor, or other mechanical or electronic device, utilizing an apparatus comprising a housing, said housing containing the device having at least one slot therein, a handle for grasping slidably disposed in said slot and secured to said housing, and a magnet for causing said handle to slide within said slot, said method comprising the steps of:
   disposing said magnet proximate said handle causing said handle to slide in said slot towards said magnet; and
   orienting said apparatus in the ear by grasping and rotating said handle.

9. A method for inserting into, orienting within, and withdrawing from an ear a hearing aid, earphone, transducer, microprocessor, radio, sensor, or other mechanical or electronic device, utilizing an apparatus comprising a housing, having at least one slot therein, said housing attached to and containing the device, a handle for grasping, slidably disposed in said slot and secured to said housing, and a magnet for causing said handle to slide within said slot, said method comprising the steps of:

inserting said apparatus into the ear by inserting the end of the housing opposite said handle into the ear;

disposing said magnet proximate said handle causing said handle to slide in said slot towards said magnet;

orienting said apparatus in the ear by grasping and rotating said handle;

pushing said handle towards said housing so that said handle slides in said slot towards said device;

disposing said magnet proximate said handle causing said handle to slide in said slot towards said magnet; and withdrawing said apparatus from the ear by grasping said handle and pulling said housing containing the device.

\* \* \* \* \*